United States Patent [19]
Salin et al.

[11] Patent Number: 5,480,809
[45] Date of Patent: Jan. 2, 1996

[54] METHOD AND APPARATUS FOR REMOVAL OF RESIDUAL INTERFERING NEBULIZED SAMPLE

[75] Inventors: Eric D. Salin, Beaconsfield; Jean-Guy J. Légère, St-Bruno, both of Canada

[73] Assignee: McGill University, Montreal, Canada

[21] Appl. No.: 281,428

[22] Filed: Jul. 27, 1994

[51] Int. Cl.$^6$ .................................................. B01D 59/44
[52] U.S. Cl. .......................... 436/173; 239/338; 250/288; 422/68.1; 436/171; 436/174; 436/180; 436/181
[58] Field of Search ...................... 436/174, 181, 436/183, 173, 171, 180; 422/68.1, 81, 82.01; 73/864.81; 239/338; 250/288

[56] References Cited

U.S. PATENT DOCUMENTS

| | | | |
|---|---|---|---|
| 4,112,297 | 9/1978 | Miyagi et al. | 250/288 |
| 4,804,519 | 2/1989 | Sainz et al. | 422/81 |
| 5,163,617 | 11/1992 | Clifford et al. | 239/338 |
| 5,259,254 | 11/1993 | Zhu et al. | 73/864.81 |
| 5,345,079 | 9/1994 | French et al. | 250/288 |

OTHER PUBLICATIONS

D. E. Dobb and D. R. Jenke, Appl. Spectrosc. 37, 379 (1983).
B. L. Sharp, J. Anal. At. Spectrom. 3, 613 (1988).
B. L. Sharp, J. Anal. At. Spectrom. 3, 939 (1988).
A. W. Varnes, J. Anal. At. Spectrom. 3, 803 (1988).
M. H. Ramsey, M. Thompson, and B. J. Coles, Anal. Chem. 55, 1626 (1983).
P. Schutyser and E. Janssens, Spectrochim. Acta Part B, 34, 443 (1979).
R. F. Suddendorf and K. W. Boyer, Anal. Chem. 50, 1769 (1978).
D. R. Luffer and E. D. Salin, Anal. Chem. 58, 654 (1986).
B. Thelin, Analyst 106, 54 (1981).
R. H. Clifford, A. Montaser, S. A. Sinex and S. G. Capar, Anal. Chem. 61, 2777 (1989).
H. Isoyama, T. Uchida, C. Iida, and G. Nakagawa, J. Anal. At. Spectrom. 5, 307 (1990).
H. Isoyama, T. Uchida, C. Iida, and G. Nakagawa, J. Anal. At. Spectrom. 4, 351 (1989).
M. Wu and G. M. Heiftje, Appl. Spectrose. 46, 1912 (1992).
D. R. Wiederin, F. G. Smith, and R. S. Houk, Anal. Chem. 63, 219 (1991).
K. E. LaFreniere, G. W. Rice, and V. A. Fassel, Spectrochim. Acta Part B, 40, 1495 (1985).
L. S. Gervais and E. D. Salin, J. Anal. At. Spectrom. 6, 41 (1991).
G. Légère and P. Burgener, ICP Inf. Newsl. 13, 521 (1988).
G. Légère and P. Burgener, ICP Inf. Newsl. 11, 447 (1985).
Guy Légère and Eric D. Salin, Applied Spectroscopy, vol. 48, No. 6, 1994, pp. 761–765.

Primary Examiner—James C. Housel
Assistant Examiner—Jan M. Ludlow
Attorney, Agent, or Firm—Bachman & LaPointe

[57] ABSTRACT

In analysis systems which employ discrete nebulized samples which are developed in a sample chamber, potentially interfering residual traces of the sample are removed in a wash-out, prior to development of a subsequent nebulized sample for analysis, in a considerably shorter time than previously possible by directing a jet of flushing gas through the chamber against the face of the nebulizer, preferably a jet of wash liquid is also directed against the nebulizer, before, after or concurrently with the jet of flushing gas.

21 Claims, 3 Drawing Sheets

METHOD AND APPARATUS FOR REMOVAL OF RESIDUAL INTERFERING NEBULIZED SAMPLE

BACKGROUND OF THE INVENTION i) Field of the Invention

This invention relates to a method of sequentially developing nebulized samples of a liquid for analysis; the invention also relates to a method of clearing potentially interfering residual sample from a sample chamber in which nebulized samples are developed, to reduce residual sample in the chamber to a background level; still further the invention relates to a method of inductively coupled plasma analysis; and to a sample chamber for development of a nebulized sample of a liquid for analysis outside the chamber.

ii) Description of Prior Art

The ability to determine many elements over a wide concentration range has made inductively coupled plasma-atomic emission spectroscopy (ICP-AES) the workhorse of elemental analysis.

Samples for analysis are typically developed in a nebulized or aerosol form in a sample chamber and the nebulized sample is then transferred from the chamber to the analysis device or equipment.

Automation can substantially reduce the need for manual labor to run the nebulized samples and improve the potential throughput of the system; however, before a fresh sample can be analyzed the effects of the last sample must be removed. The time taken to reduce the signal from residual sample so that it will not compromise the measurement of the analyte signal of the subsequent sample to be analyzed is called "wash-out time".

A wash-out time sufficient to deal with the largest concentration difference that might arise between contiguous samples is used for most applications. In an environmental laboratory this could be as long as ten minutes, but generally a two minute wash-out is used after which data are reviewed and suspect samples rerun.

Polychromators and some ICP-MS (Mass Spectrometry) spectrometers can perform their analyses in approximately 10 seconds, while the wash-out time for commercial and even experimental nebulizer sample introduction generally ranges from 30 seconds to 4 minutes. Dobb and Jenke, Appl. Spectrosc. 1983, 37, 379, report that rigorous correction for the memory by allowing for sufficient sample washout ($T_{0.01}$) increases analysis time per sample by a factor of 5. Clearly, a significant improvement in wash-out time could drastically affect the throughput of ICP based systems.

Many ways have been suggested to evaluate wash-out time. The evaluation criteria which have been suggested differ significantly and require that one apply considerable caution in comparing the results.

Wash-out time can be the time required for the signal to approach an arbitrarily selected value after aspirating a randomly selected sample solution. The word "arbitrary" is used to indicate that there is no fundamental relationship to dictate testing criteria.

A more precise definition of wash-out time proposed by R. M. Clifford et al, Anal. Chem. 1989, 61, 2777, requires reduction of the signal of residual sample to the 1% level, after an analyte solution is replaced with a blank solution (time of exchange). The actual moment to start timing is the instant of exchange, but some authors use the first sign of signal decay from the steady-state value. Measuring wash-out time from the time of exchange is more realistic in evaluating sample throughput. If the analyte level of the samples varies over several orders of magnitude, samples with relatively low levels that follow samples at very high levels will be biased high unless the wash-out time is increased considerably. Another definition of wash-out time uses a solution that is at least five orders of magnitude above the limit of detection for the particular element of interest. Typically a 1000 μg/g pure stock solution is used and replaced with a blank. The wash-out time is measured from the time of exchange until a signal level equivalent to ±0.01 μg/g of the original analyte signal level is reached. When the first definition (1%) is used to evaluate wash-out time, a time of 20 seconds to several minutes can be obtained, but when the latter definition is used, wash-out times of an order of magnitude longer are possible. For the comparison of two systems, a wash-out to 1% of the original signal level is useful, but, for analyses, any measurable trace of previous analyte must be removed.

It is clearly desirable to decrease the wash-out time to improve efficiency. It has been suggested that there are at least four major causes of long wash-out times in spray chambers which include dead volumes in the nebulizer tubing, adsorption and subsequent slow release of residual sample by the nebulizer tubing, size of the sample development chamber or spray chamber, dead volume in the spray chamber, entrainment of residual sample by gas issuing from the nebulizer and reaspiration of the entrained sample.

Thus far efforts to reduce wash-out time by approaches directed to these causes have not met with any significant success.

SUMMARY OF THE INVENTION

It is an object of this invention to provide a method of clearing potentially interfering residual sample from a sample chamber in which nebulized samples are developed, with a shortened wash-out time.

It is a further object of the invention to provide a method of sequentially developing nebulized samples of a liquid for analysis exploiting a short wash-out time between nebulized sample development.

It is a still further object of the invention to provide a method of inductively coupled plasma analysis which exploits the short wash-out time of the sample chamber, prior to development of a fresh nebulized sample.

It is yet another object of the invention to provide a sample chamber for development of a nebulized sample of a liquid for analysis outside the chamber, with provision for a short wash-out time.

The invention provides in one aspect a method of sequentially developing nebulized samples of a liquid for analysis in which a) there is provided a source of nebulized sample in a chamber; b) a nebulized sample of liquid is formed in the chamber at the source; c) the bulk of the nebulized sample is removed from the chamber, with retention in the chamber of a residual amount of the sample effective to provide a detectable level of the sample, in the chamber, above a background level; d) at least one jet of flushing gas is directed against the source, the jet being effective to flush out residual nebulized sample in the chamber; and e) steps b), c) and d) are repeated sequentially with different liquid samples.

In particular the jet of flushing gas removes residual sample, typically in droplet form, from the source, and more especially flushes out residual aerosol in the atmosphere of the chamber.

A plurality of jets of flushing gas may be directed against the source from different locations within the chamber, so as to facilitate formation of a turbulent flow of flushing gas to sweep out the residual aerosol in the atmosphere of the chamber.

While the use of one or more jets of flushing gas is found to provide a shortening of the wash-out time, a more significant and reliable shortening of the wash-out time is achieved in the method if at least one jet of wash liquid is directed against the nebulizing source, the at least one jet of wash liquid being effective to entrain the residual sample on the nebulizing source, a mixture of wash liquid and entrained sample being collected in a well in the floor of the chamber below the source, the mixture being drained from the well. In this method the at least one jet of flushing gas is directed against the source after, before or simultaneously with the at least one jet of wash liquid.

Conveniently the jets of flushing gas and wash liquid are directed against the source from a single nozzle in opposed spaced apart relationship with the source, and the nozzle is spaced from the source so as to be disposed outside a nebulizing zone of the source. In this case the wash liquid is preferably directed against the source, and thereafter the flushing gas is directed against the source; but the sequence can be reversed so that the flushing gas is followed by the wash liquid. The wash liquid and the flushing gas could also be directed against the source from separate nozzles, or a plurality of jets of one or both of the wash liquid and the flushing gas can be directed against the source from separate nozzles. While it is especially preferred that at least one jet of the flushing gas be directed against the nebulizing source from a nozzle in opposed spaced apart relationship with the source, this opposed spaced apart relationship is less important for the jet or jets of wash liquid.

In another aspect of the invention there is provided a method of washing out a sample chamber having a nebulizer for development of a nebulized sample of a liquid, to reduce residual sample leaving the chamber to a background level comprising directing at least one jet of wash liquid against a nebulized sample outlet of the nebulizer, directing at least one jet of flushing gas against said nebulizer from a position in generally opposed spaced apart relationship with the nebulized sample outlet, to flush out residual nebulized sample, collecting a mixture of the wash liquid and residual sample in a well in a floor of the chamber, said well being disposed vertically below said outlet, and draining the mixture from said well.

This latter method can also be carried out without the use of the jet or jets of wash liquid, but significantly better results in terms of a significant and reliable shortened wash-out time are achieved employing both the jet or jets of wash liquid and the jet or jets of flushing gas.

As described previously, where both wash liquid and flushing gas are directed against the nebulizer, the flushing gas may be directed against the nebulizer before, after or concurrently with the wash liquid, but preferably the flushing gas is directed against the nebulizer after the wash liquid.

In the method of the invention residual sample which is removed from the chamber is sample which might otherwise be transferred to the analysis device with a subsequent nebulized sample.

The jet of flushing gas forms a turbulent flow in the chamber and sweeps residual aerosol from the atmosphere of the chamber, the residual aerosol being swept out of the chamber at the sample exit of the chamber.

It will be understood that the nebulized form of the sample is an aerosol which may fill the atmosphere of the chamber.

The jet of flushing gas also functions to remove residual sample and additionally residual wash liquid from the face of the nebulizing source.

In a particular aspect of the invention there is provided in a method of inductively coupled plasma analysis in which discrete nebulized samples of a liquid are developed in a sample chamber for analysis and in which a wash out of the sample chamber is carried out after removal of a discrete nebulized sample from the chamber and prior to development of a subsequent discrete nebulized sample, the improvement in which at least one jet of wash liquid is directed against a source of the discrete nebulized sample, at least one jet of flushing gas is directed against said source from a position in generally opposed spaced apart relationship with said source to flush out residual nebulized sample, a mixture of said wash liquid and residual sample is collected in a well in a floor of the chamber, said well being vertically below said source, and the mixture is drained from the well.

In still another aspect of the invention there is provided a sample chamber for development of a nebulized sample of a liquid for analysis outside the chamber comprising a chamber housing having a chamber floor, a nebulizer mounted in said housing, said nebulizer having an outlet for nebulized sample, nozzle means for directing a jet of wash liquid and a jet of flushing gas against said nebulizer, said nozzle means comprising a nozzle mounted in said housing in generally opposed, spaced apart relationship with said outlet, and a well defined in said floor vertically below said outlet.

The wash liquid may suitably comprise the vehicle employed for the sample but this is not essential; it will be understood that the wash liquid should be free of the sample and components of the sample, or other components which might interfere with the analysis results or produce a misleading result.

The flushing gas is conveniently an inert gas such as argon.

BRIEF DESCRIPTION OF THE DRAWINGS

The invention is illustrated in particular and preferred embodiments by reference to the drawings in which.

DESCRIPTION OF PREFERRED EMBODIMENT WITH REFERENCE TO THE DRAWINGS

Figure 1:
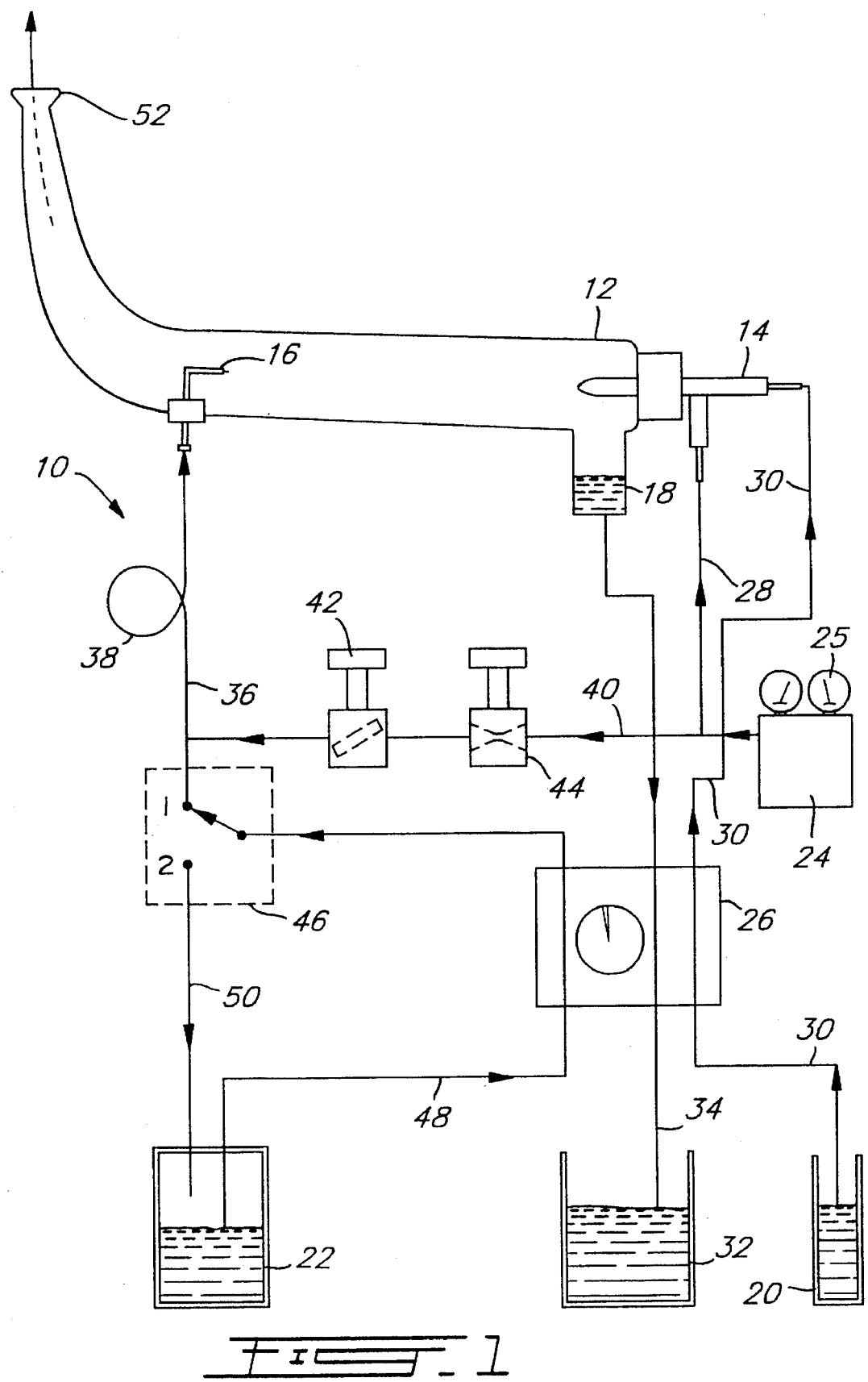
FIG. 1 illustrates schematically a sample chamber for development of a nebulized sample of a liquid for analysis outside the chamber, in accordance with the invention.

With further reference to FIG. 1, there is shown schematically a rapid clearing spray chamber assembly 10 of the invention.

Assembly 10 includes a spray chamber 12, a nebulizer 14, a flush nozzle 16 and a drain 18.

Assembly 10 further includes a sample source 20, a wash solution reservoir 22, a gas source 24, a regulator 25 and a pump 26.

A gas line 28 communicates gas source 24 and nebulizer 14.

A sample line 30 communicates sample source 20 and nebulizer 14.

Drain 18 communicates with a waste collector 32 via a waste line 34.

A wash line 36 communicates with nozzle 16 and includes a wash loop 38.

A gas flush line 40 connects between regulator 25 and wash line 36, and includes a flush valve 42 and a restrictor 44.

A three-way valve 46 is disposed in wash line 36 upstream of the junction with gas flush line 40.

Wash line 36 includes a wash load line 48 between reservoir 22 and valve 46 and a wash return line 50 between valve 46 and reservoir 22.

The spray chamber 12 has a chamber outlet 52 communicating with an analysis device (not shown).

The gas source 24 incorporates the regulator 25 which feeds the gas under pressure into gas line 28 or gas flush line 40.

Pump 26 operates to pump a sample to be analyzed from source 20 to nebulizer 14 and also to pump wash solution along wash load line 48 to wash loop 38 via valve 46. It will be understood that separate pumps could be employed for the sample and the wash solution.

In operation a sample to be analyzed is pumped by pump 26 from source 20 to nebulizer 14 and gas is passed by regulator 25 from source 24 so that an aerosol of the sample is ejected from nebulizer 14 into spray chamber 12, which aerosol is passed through chamber outlet 52, the sample exit port of the chamber 12, into an analysis device (not shown).

Before a second sample can be introduced into the spray chamber 12, residual amounts of the aerosol which would contaminate the subsequent sample aerosol and provide erroneous analysis results, need to be removed at least to a background level of the analysis.

In accordance with the invention the three way valve 46 is shifted to position 1 and wash solution is pumped from reservoir 22 by pump 26 into wash line 36 to fill wash loop 38. When wash loop 38 is filled, valve 46 is shifted to position 2 so that wash solution in load line 48 is returned by return line 50 to reservoir 22. When required flush valve 42 is opened and gas under pressure from gas source 24 forces the wash solution as a jet from nozzle 16, the jet being directed towards the face of nebulizer 14, the wash liquid with entrained residual sample is allowed to flow by gravity into drain 18 and thence through waste line 34 to waste collector 32. Thereafter, flushing gas is directed from source 24 through lines 40 and 36 and emerges as a jet from nozzle 16, which jet is directed against the face of nebulizer 14.

This jet of flushing gas particularly flushes out sample aerosol from the chamber, but also flushes out liquid on the face of nebulizer 14, which liquid may include wash liquid and residual sample in liquid form.

Suitably this jet of flushing gas is delivered as a short pulse of gas whereafter the wash liquid with entrained sample or liquid sample, from the face of nozzle 16, is allowed to flow by gravity into drain 18 and a further jet of flushing gas is delivered from nozzle 16 as a short pulse.

The nozzle 16 is particularly located in opposed spaced apart relationship with the face of nebulizer 14 and is spaced so that the nozzle 16 is outside the nebulizing zone of nebulizer 14.

In a preferred embodiment the jet of flushing gas is directed in a pulse form, typically two pulses, with the interval between the pulses being sufficient to allow time for wash liquid and entrained sample as well as liquid sample to collect in drain 18 under gravity. In this way, aerosol of the wash solution with entrained sample is not formed.

The flushing gas flows as a jet from nozzle 16 to the face of nebulizer 14 and in a turbulent flow is deflected back towards nozzle 16 and then exits chamber 12 through chamber outlet 52. The flushing gas entrains residual aerosol in the atmosphere of the chamber and flushes such residual aerosol from the chamber. By employing at least a second flow of flushing gas as a jet from nozzle 16 at a time interval after a first flow, one ensures that an efficient flushing of the aerosol is achieved.

EXPERIMENTAL

Reagents

The solutions used in measuring wash-out times were made from 1000 µg/g ferric nitrate in 2% nitric acid and 1000 µg/g zinc oxide in 5% nitric acid both from Fisher Scientific. The Fe and Zn were mixed 1:1 and measured simultaneously. Two percent nitric acid solution W/W made from distilled/deionized water and concentrated nitric acid (J. T. Baker) was used as the rinse solution and for dilution of the Fe/Zn solutions.

Spectrometer and Source

A Plasma Therm torch of the type described by Gervais and Salin, J.Anal. St Spectrom., 1991, 6, 41, was used to minimize any disturbance that might be caused by high gas flows through the center of the plasma. The plasma was operated at 1.0 kW forward power with a plasma gas of 17.0 l/min. and an auxiliary gas flow of 0.9 l/min. A Plasma Therm RF generator HFP 2500D and crystal controller APCS-1 supplied power to a three turn coil. The spectrometer, a Jarrell Ash Model 750, was refitted as described in Légère and Burgener in ICP Inf. Newslr. 1988, 12, 521, to place a scanning quartz behind the entrance slit and replace all data acquisition software and hardware. The refitted system allowed transient data acquisition, on and off line, for eight channels simultaneously at a rate of up to 300 Hz. Fe was measured at 259.94 nm and Zn at 213.85 nm (both in the first order) at a viewing height in the plasma of 15 mm above the load coil. Nebulizers were fed with a MiniPuls (trademark of Gilson) 2 peristaltic pump at 2 mL/min. (Normal) or 4.0 mL/min. (Fast).

Data Acquisition

Data was acquired in two modes. In the on-line mode (spectrum shifter not utilized) the data acquisition rate was 0.83 Hz. In the background correction mode data was collected at 0.6 s. intervals in an on-line off-line sequence. Background corrected values were obtained by subtracting the off-line value from the on-line value. Each run lasted 76.8 s. with a total of 128 data points for each channel. Data for the Fe and Zn channels were obtained simultaneously on all data acquisition runs.

Spray Chamber and Nebulizer

A traditional Scott double-pass spray chamber (100 mL) fitted with a Meinhard C-type nebulizer was used inside the Plasma Therm source box as the standard configuration. This is referred to as the "conventional spray chamber".

The rapid clearing spray chamber assembly of the invention, illustrated in FIG. 1, was tested with the Meinhard C nebulizer and the Légère V-groove nebulizer described by Légère and Burgener in ICP Inf. Newsl., 1985, 11, 447. The straight-through spray chamber nebulizer 12 was mounted underneath the source box to accommodate its longer length. The spray chamber 12 had a volume of 294 mL. The main feature was the 1/16 stainless steel flush nozzle 16 mounted 17 cm in front of the face of the nebulizer 14. A jet of Ar or wash solution was directed at the face of the nebulizer 14 from the nozzle 16. Wash loop 38 was a 4.5 mL, 1.58 mm ID wall PFA tube. The input of the wash loop 38 forms a T junction with the gas flush line 40 and position "1" of the three way valve 46. The three way valve 46 can direct wash solution from reservoir 22 to position "1" to load the wash loop 38 or position "2" to return the wash solution to the reservoir 22. Once the wash loop 38 has been filled the three way valve 46 is switched to position "2" and the flush valve 42 opened to wash out the spray chamber 12 with wash solution forced under pressure from nozzle 16 as a jet against nebulizer 14. Wash solution was forced through the nozzle 16 onto the face of nebulizer 14 by the gas pressure followed by a timed blast of argon gas (9.6 l/min.). Restrictor 44 in the gas flush line 40 allowed adjustment of the nozzle flow rate at a fixed input pressure of 100 psi.

Wash-out Sequence

All valve switching was done manually in three experiments. The 500 mg/g Fe/Zn solution was pumped to the nebulizer 14 at the "Normal" pump speed of 60 s. to insure maximum and steady state analyte levels for the start of the wash-out sequence. Simultaneously the wash loop 38 was filled and the three way valve 46 returned to position "2". The wash-out sequence began when the Fe/Zn solution was replaced with the reagent blank, called "time of exchange", and the pump 26 switched to "Fast" speed. The reagent blank took 7 s. after the exchange to reach the spray chamber 12 at which time the gas restrictor 44 was opened for 5 s. closed for 1 s. and reopened for another 5 s.

Wash-out Time Calculation

The wash-out time was measured from the time of exchange to the time at which the analyte signal had an average value equivalent to that of the background signal.

RESULTS

Figure 2:
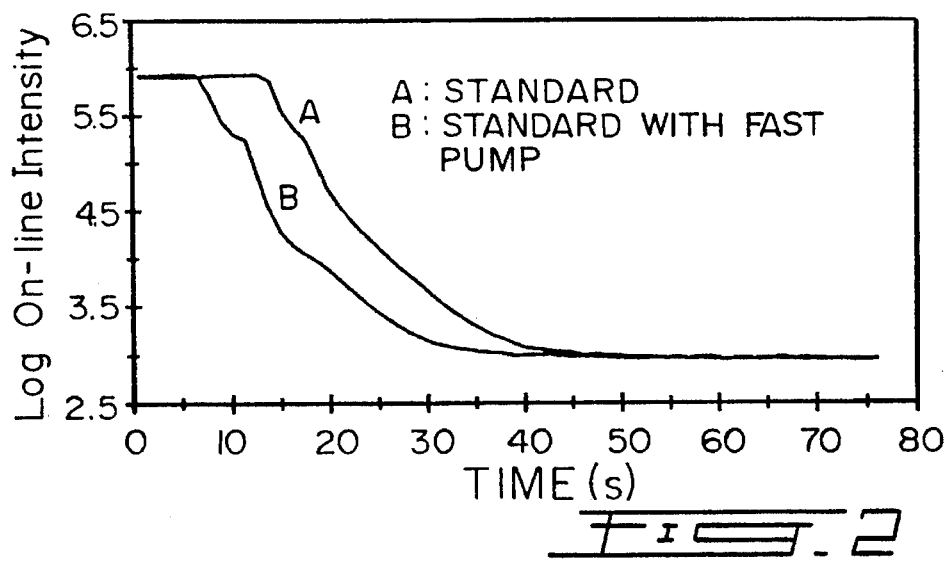
FIG. 2 illustrates graphically the wash-out response in a conventional spray chamber system using a low pump speed (plot A) and a high pump speed (plot B) for the wash solution.

In FIG. 2 the wash-out response for the conventional system is plotted as the on-line intensity for Fe on a logarithmic scale. Fe was chosen for this study because it is often high in concentration and interferes spectrally for many elements. When Zn was used instead of Fe the same effects were observed for both nebulizers. The detection limit (3 standard deviations) for Fe was 10 ppb for the relatively short exposure time of 0.6 seconds per position. Curve "A" and Curve "B" of FIG. 2 show the wash-out response after the sample was replaced with a reagent blank. The "Normal" pump speed was used for Curve "A" and "Fast" speed for Curve "B". The logarithmic plot allows one to evaluate the performance over the entire range used and gives a more accurate overall picture. A linear plot provides a sharp drop in intensity giving the false impression that the analyte signal had reached the background level rapidly. Visual inspection of the curves shows that the "Fast" pump speed, Curve "B" seems to give faster wash-out.

Figure 3:
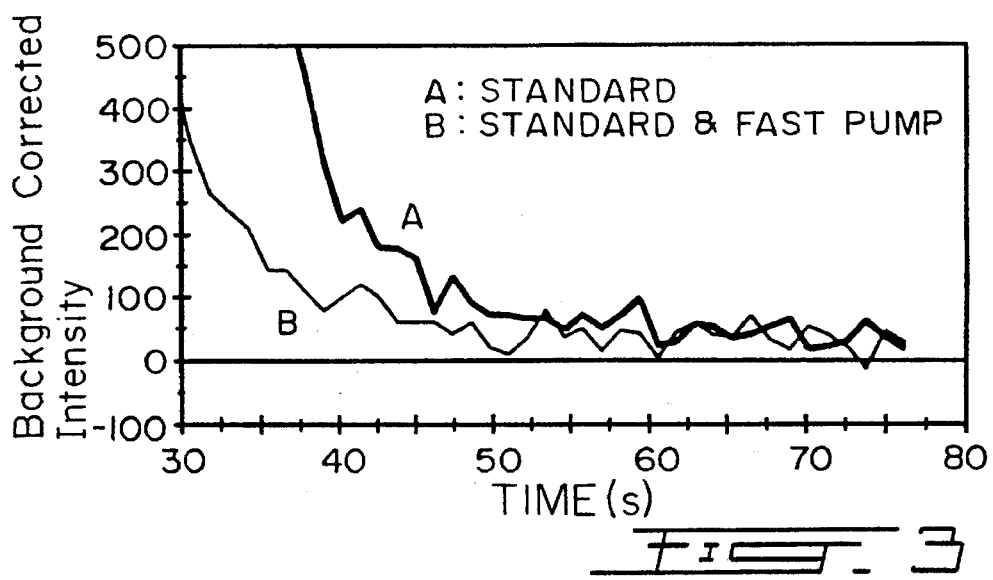
FIG. 3 shows graphically the data of FIG. 2 as the signal levels approach that of a blank.

It was very informative, however, to take a closer look as the signal level approaches that of a blank. The on-line/off-line capability of the spectrometer allowed rapid background corrected measurements. This data provided a much clearer picture as the baseline was approached. When the signal approached background level it was important to subtract the off-line intensity from the on-line intensity to account for any drift in background intensity. In FIG. 3, the background corrected intensities (linear scale) of Curve "A" and Curve "B" after 30 s. are plotted versus time in seconds. When the background corrected intensity averages zero the background level has been reached and wash-out is complete. The integration time was 1.8 s. and therefore the results would not be as precise as would a normal integration time of 10–15 s. In FIG. 3 the wash-out has not reached background level even after 75 s. The figure also reveals that there is no real difference after 55 s. between Curves "A" and "B", demonstrating that doubling the volume of wash solution (Curve "B") is not a critical factor in wash-out of a sample to background levels.

In order to compare the conventional Scott spray chamber to the rapid clearing assembly in FIG. 1, both nebulizer types (Meinhard and Légère V-groove) were tested in the same manner as the conventional system. The intensity profiles for the wash-out trials are plotted in FIG. 4 for the Meinhard and FIG. 5 for the Légère V-groove. One wash-out was done with the pump speed at normal speed, Curve "A", and a second was performed at fast pump speed, Curve "B". The rapid clearing spray chamber trends are similar to those seen on the conventional system but the actual wash-out times for the assembly are longer than the conventional spray chamber, probably due to its large size of 294 mL compared to 100 mL for the Scott spray chamber.

The first prototype used a conical gas sheath around the head of a Légère V-groove nebulizer with the direction of the gas flow towards the exhaust end of the spray chamber. The spray chamber cleared of all aerosol and the analyte signal level dropped to background levels quickly, but large erratic increases in signal (spikes) due to the reaspirated analyte were seen a full 60 s. after the gas flow had returned to normal levels.

The assembly 10 in FIG. 1 has the wash-out gas in the reverse direction allowing it to flush out dead volume to the side and behind the nebulizer 14. If aerosol left in the spray chamber 12 was the only source of memory this arrangement would be completely effective in reducing the analyte signals to background levels. The rapid clearing out scheme of Curve "B", FIGS. 4 and 5, was repeated with the addition of a 5 s. gas flush. The results are plotted as Curve "C", FIGS. 4 and 5. Curve "C" dropped well below the background level when the gas was turned on and returned to near background levels when the gas was turned off. However, after the flush gas was turned off the analyte signal for the Meinhard still continued a slow downward trend to background level and the Légère nebulizer experienced sharp rises in analyte signal even after 75 s. Examination of the Légère V-groove nebulizer face revealed droplets that could flow across the nebulizer face and be reaspirated.

Increasing the length of the gas flush did not improve the performance of the system. These first experiments demonstrate that high gas volumes alone would not solve the problem. Several other factors proved to be important.

Employing the assembly 10 of the invention in FIG. 1 the wash loop 38 was loaded with 2% nitric acid solution and sprayed onto the face of nebulizer 14 when the flush valve 42 was turned on. The flush valve 42 is turned on with the three way valve 46 in position "2" which keeps gas from being blown into the tubing of pump 26 and avoids stopping the pump 26 after the wash loop 38 is loaded. The rapid clearing cycle was started by switching the pump speed to "Fast" and then opening the flush valve 42 to force the wash solution out through the nozzle 16 onto the face of the nebulizer 14. Then the wash solution flows by gravity to the large drain 18 out of the path of the following flush gas burst. The removal of the wash solution is critical since the wash solution would otherwise be entrained in the gas flush, creating large amounts of aerosol. The large drain 18 does this more effectively than a high speed peristaltic pump. The flush gas is turned on for 5 s. and turned off momentarily to allow any liquid that is being pushed up the torch end of the spray chamber to flow down to the drain 18 and then turned back on for another 5 s. to finish the cycle.

Figure 4:
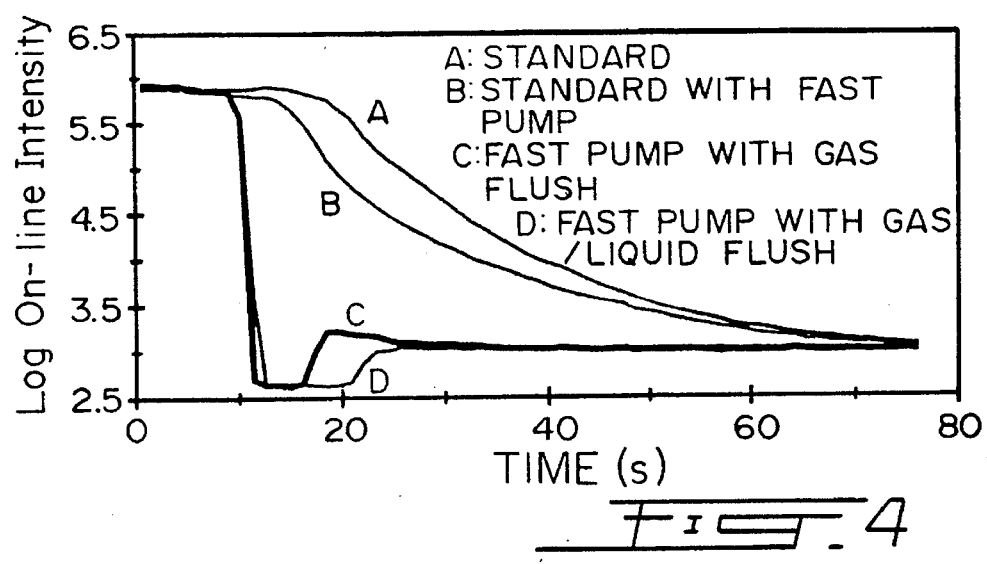
FIG. 4 compares graphically intensity profiles for wash-out using the conditions of FIG. 2 (plots A and B) with the addition of flushing gas, from the nebulizer, to the profile of plot B (plot C), and the system of the invention (plot D), using a first type of nebulizer, with wash liquid and flushing gas being directed against the nebulizer.
Figure 5:
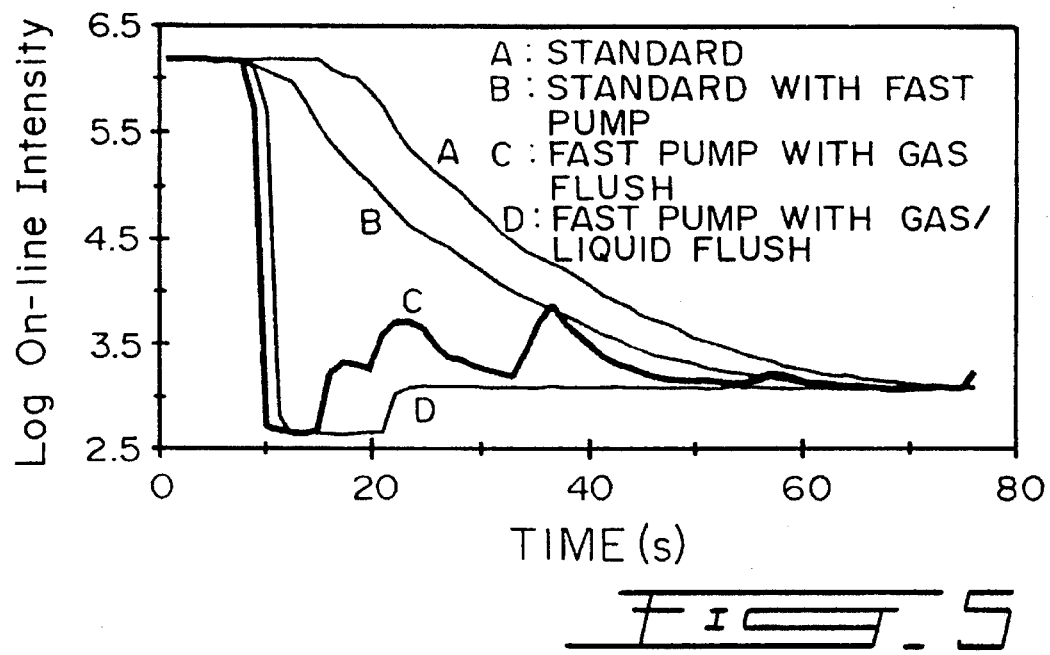
FIG. 5 is similar to FIG. 4 but employing a second type of nebulizer.

The rapid clearing spray chamber response for the combination of fast pump speed, gas flush and wash solution sprayed on the nebulizer face is plotted in FIGS. 4 and 5 as Curve "D". After the gas flush cycle is completed the signal levels for both nebulizers were at background levels with no erratic signals as was evident when the gas flush was used without the wash solution (Curve "C"). Consequently wash-out from a starting concentration of 500 mg/g to a detection limit of approximately 10 ppb, a factor of $5 \times 10^4$ was achieved.

Figure 6:
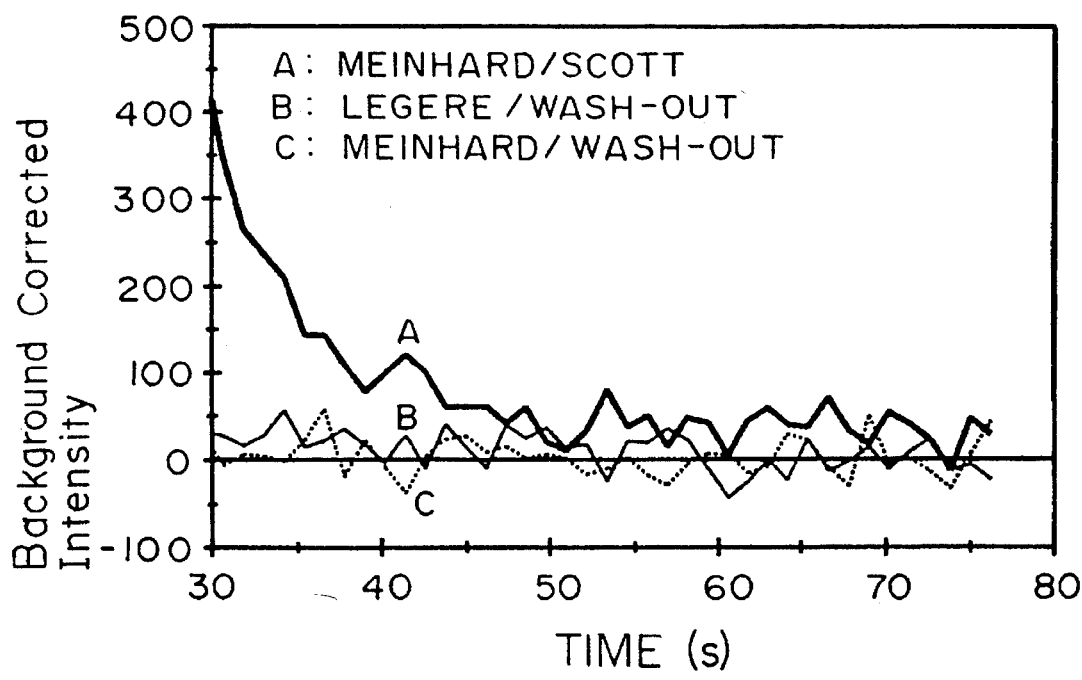
FIG. 6 illustrates graphically background levels achieved by the conventional system (plot A) and rapid clearing systems of the invention (plots B and C) with different nebulizers.

The effectiveness of the rapid clearing system of the invention is made even more evident when background level values after the gas flush and wash are compared to background levels when the conventional system is used. Curve "A" of FIG. 6 is the conventional system using a fast pump speed to wash-out. Curves "B" and "C" of FIG. 6 are the rapid clearing curves for the Meinhard and Légère nebulizers, respectively. Note that the signal levels averaged zero almost immediately whereas the conventional system still had not reached this level after 76 s.

The last trial of the rapid clearing system used a 1% copper solution. After aspiration of the copper solution for 60 s. blue droplets formed on the inside walls of the spray chamber and the nebulizer face. The rapid clearing cycle of the invention removed blue droplets that had formed on the nebulizer face but failed to remove the blue droplets from the walls of the spray chamber. However, no evidence of copper was present in the analyte signal after the wash-out cycle.

We claim:

1. A method of sequentially developing nebulized samples of a liquid for analysis comprising:
   a) providing a nebulizer means in a chamber, said nebulizer means including means for supplying sample, said nebulizer means being disposed above a floor of said chamber,
   b) forming a nebulized sample of a liquid with said nebulizer means, in said chamber,
   c) removing the bulk of said nebulized sample from said chamber, with retention in said chamber of a residual amount of said sample, said residual amount being effective to provide a detectable level of the sample, in said chamber, above a background level,
   d) directing at least one jet of wash liquid against said nebulizer means, said jet being effective to entrain residual sample, collecting a mixture of wash liquid and entrained sample in a well in said floor, below said nebulizer means, and draining said mixture from said well,
   e) directing at least one jet of flushing gas against said nebulizer means, said jet of flushing gas being effective to flush out residual nebulized sample in said chamber, and
   f) repeating steps b), c), d) and e) sequentially with different liquid samples.

2. A method according to claim 1, wherein at least one jet of flushing gas in e) is directed against said nebulizer means from a nozzle in opposed spaced apart relationship with said nebulizer means.

3. A method according to claim 2, wherein said nozzle is spaced from said nebulizer means so as to be disposed outside a nebulizing zone of said nebulizer means.

4. A method according to claim 1 wherein step e) follows step d).

5. A method according to claim 1 wherein steps d) and e) are carried out concurrently.

6. A method according to claim 1 wherein step d) follows step e).

7. A method according to claim 2 wherein the jet of flushing gas is delivered in a pulse form, and said flushing gas develops a turbulent flow in said chamber effective to entrain residual nebulized sample and convey the entrained residual nebulized sample through a sample exit of said chamber.

8. A method of washing out a sample chamber having a nebulizer for development of a nebulized sample of a liquid, said nebulizer including means for supplying sample, said method comprising:

directing at least one jet of wash liquid against said nebulizer, directing at least one jet of flushing gas against said nebulizer from a position in generally opposed spaced apart relationship with a nebulized sample outlet of said nebulizer, to flush out residual nebulized sample, collecting a mixture of the wash liquid and residual sample in a well in a floor of the chamber, said well being disposed vertically below said outlet, and draining the mixture from said well.

9. A method according to claim 8 wherein said position is outside a nebulizing zone of said nebulizer.

10. A method according to claim 8 wherein the jet of flushing gas is delivered in a pulse form, in which the pulses are at intervals to allow time for mixture of wash liquid and entrained sample to collect and drain, under gravity, from said chamber.

11. A method according to claim 8 wherein said at least one jet of flushing gas is directed against said nebulizer after said at least one jet of wash liquid.

12. In a method of inductively coupled plasma analysis in which discrete nebulized samples of a liquid are developed by a nebulizer means in a sample chamber for analysis and in which a wash out of the sample chamber is carried out after removal of a discrete nebulized sample from the chamber and prior to development of a subsequent discrete nebulized sample, said nebulizer means including means for supplying sample the improvement in which at least one jet of wash liquid is directed against said nebulizer means, at least one jet of flushing gas is directed against said nebulizer means from a position in generally opposed spaced apart relationship with said nebulizer means, to flush out residual nebulized sample, a mixture of said wash liquid and residual sample is collected in a well in a floor of the chamber, said well being vertically below said nebulizer means, and the mixture is drained from the well.

13. A method according to claim 12 wherein said at least one jet of flushing gas is directed against said nebulizer means after said at least one jet of wash liquid.

14. A method according to claim 12 wherein said analysis comprises atomic emission spectroscopy of nebulized sample.

15. A method according to claim 12 wherein said analysis comprises mass spectroscopy of nebulized sample.

16. A method according to claim 12 wherein the at least one jet of flushing gas is delivered in a pulse form, in which the pulses are at intervals to allow time for mixture of wash liquid and entrained sample to collect and drain, under gravity, from said chamber.

17. A sample chamber for development of a nebulized sample of a liquid for analysis outside the chamber comprising:
   a chamber housing having a chamber floor,
   a nebulizer mounted in said housing, said nebulizer including means for supplying sample, said nebulizer having an outlet for nebulized sample,
   nozzle means for directing a jet of wash liquid and a jet of flushing gas against said nebulizer, said nozzle means comprising a nozzle mounted in said housing in generally opposed, spaced apart relationship with said outlet, and
   a well defined in said floor vertically below said outlet.

18. A chamber according to claim 17 further including pump means, a regulator and associated valve and conduit means in fluid communication for pumping a liquid to be analyzed to said nebulizer, and for pumping a wash liquid and a flushing gas from said nozzle means as jets under pressure.

19. A method of sequentially developing nebulized samples of a liquid for analysis comprising:
   a) providing a nebulizer means in a chamber, said nebulizer means being disposed above a floor of the chamber,
   b) forming a nebulized sample of a liquid at said nebulizer means, in said chamber,
   c) providing a gas stream in a first direction to remove the bulk of said nebulized sample from said chamber, with retention in said chamber of a residual amount of said sample, said residual amount being effective to provide a detectable level of the sample, in said chamber, above a background level,
   d) directing at least one jet of flushing gas in a second direction against said nebulizer means, from a position in generally opposed spaced apart relationship with said nebulizer means, said jet being effective to flush out nebulized residual sample, and
   e) repeating steps b), c) and d) sequentially with different liquid samples.

20. A method according to claim 19 wherein said position is spaced from said nebulizer means, to be disposed outside a nebulizing zone of said nebulizer means.

21. In a method of inductively coupled plasma analysis in which discrete nebulized samples of a liquid are developed by nebulizer means in a sample chamber for analysis and in which a wash out of the sample chamber is carried out after removal of a discrete nebulized sample from the chamber by a stream of gas provided in a first direction and prior to development of a subsequent discrete nebulized sample, the improvement in which
   a jet of flushing gas is directed in a second direction against said nebulizer means, from a position in generally opposed spaced apart relationship with said nebulizer means, said jet being effective to flush out residual nebulized sample.

* * * * *